United States Patent
Reneker et al.

(10) Patent No.: US 9,328,433 B2
(45) Date of Patent: May 3, 2016

(54) METHOD OF CHARACTERIZATION OF VISCOELASTIC STRESS IN ELONGATED FLOW MATERIALS

(71) Applicants: Darrell H. Reneker, Akron, OH (US); Tao Han, Akron, OH (US); Alexander L. Yarin, Clarendon Hills, OH (US)

(72) Inventors: Darrell H. Reneker, Akron, OH (US); Tao Han, Akron, OH (US); Alexander L. Yarin, Clarendon Hills, OH (US)

( * ) Notice: Subject to any disclaimer, the term of this patent is extended or adjusted under 35 U.S.C. 154(b) by 84 days.

(21) Appl. No.: 14/139,938

(22) Filed: Dec. 24, 2013

(65) Prior Publication Data

US 2014/0284828 A1    Sep. 25, 2014

Related U.S. Application Data

(62) Division of application No. 12/741,836, filed as application No. PCT/US2008/012639 on Nov. 10, 2008, now Pat. No. 8,636,493.

(60) Provisional application No. 60/986,371, filed on Nov. 8, 2007.

(51) Int. Cl.
   *B29C 47/92* (2006.01)
   *D01D 7/00* (2006.01)
   *D01D 5/00* (2006.01)
   *G01N 11/02* (2006.01)
   *G01N 11/00* (2006.01)

(52) U.S. Cl.
   CPC .............. *D01D 5/0069* (2013.01); *D01D 5/003* (2013.01); *D01D 5/0023* (2013.01); *D01D 5/0076* (2013.01); *D01D 5/0092* (2013.01); *G01N 11/02* (2013.01); *G01N 2011/0026* (2013.01); *G01N 2011/0073* (2013.01)

(58) Field of Classification Search
   CPC .... B29C 47/92; D01D 5/0007; D01D 5/0015; D01D 5/0023; D01D 5/003; D01D 5/0038; D01D 5/0046; D01D 5/0061; D01D 5/0076; D01D 5/0092; D01D 7/00
   USPC ............. 264/10, 40.1, 211.12, 464, 465, 466, 264/484
   See application file for complete search history.

(56) References Cited

U.S. PATENT DOCUMENTS

| | | | | |
|---|---|---|---|---|
| 2,954,271 | A | * | 9/1960 | Cenzato .................... 264/464 X |
| 2007/0018361 | A1 | * | 1/2007 | Xu ................................ 264/465 |
| 2009/0130301 | A1 | * | 5/2009 | Bahnmuller et al. ......... 427/122 |

FOREIGN PATENT DOCUMENTS

KR       100662091 B1 * 12/2006
WO    WO-2007084742 A2 *  7/2007

* cited by examiner

*Primary Examiner* — Leo B Tentoni
(74) *Attorney, Agent, or Firm* — Renner Kenner Greive Bobak Taylor & Weber (57) ABSTRACT

The present invention generally relates to a device for measuring characteristics of polymeric fluids (semi-dilute and concentrated polymer solutions and melts) in extremely strong elongational flows. In one embodiment, the present invention relates to a device for measuring characteristics of polymeric fluids (semi-dilute and concentrated polymer solutions and melts) in extremely strong elongational flows in spinning jets and/or electrified jets. In another embodiment, the present invention relates to a method for determining the elastic modulus and the relaxation time of a polymeric fluid. Also, the present invention enables one to determine and/or measure the primary parameters needed to describe a viscoelastic material.

23 Claims, 10 Drawing Sheets

METHOD OF CHARACTERIZATION OF VISCOELASTIC STRESS IN ELONGATED FLOW MATERIALS

CROSS REFERENCE TO RELATED APPLICATIONS

This application is a divisional of U.S. application Ser. No. 12/741,836 entitled "Method of Characterization of Viscoelastic Stress in Elongated Flow Materials," filed Apr. 14, 2011, now U.S. Pat. No. 8,636,493, which claims the benefit International application No. PCT/US2008/012639 entitled "Method of Characterization of Viscoelastic Stress in Elongated Flow Materials," filed Nov. 10, 2008, which claims the benefit of U.S. provisional patent application Ser. No. 60/986,371, filed Nov. 8, 2007, and incorporated herein by reference in its entirety.

FIELD OF THE INVENTION

The present invention generally relates to a device for measuring characteristics of polymeric fluids (semi-dilute and concentrated polymer solutions and melts) in extremely strong elongational flows. In one embodiment, the present invention relates to a device for measuring characteristics of polymeric fluids (semi-dilute and concentrated polymer solutions and melts) in extremely strong elongational flows in spinning jets and/or electrified jets. In another embodiment, the present invention relates to a method for determining the elastic modulus and the relaxation time of a polymeric fluid. Also, the present invention enables one to determine and/or measure the primary parameters needed to describe a viscoelastic material.

BACKGROUND OF THE INVENTION

Polymeric viscoelastic liquid jets represent key elements of such technologies as textile fiber spinning and electrospinning, as well as in some other applications. Such jets can sustain significant longitudinal stresses of viscoelastic origin. In fiber spinning, aerodynamic jet bending and electrospinning of viscoelastic liquids, both stretching and relaxation are present. The longitudinal stress level is determined by the competition between the stretching and relaxation. Moreover, in the electrically-driven jets in electrospinning the longitudinal viscoelastic stresses begin to build up in the orifice, and become large in the transition zone from the Taylor cone to a completely formed jet. Therefore, viscoelastic jets can possess both significant initial longitudinal viscoelastic stresses generated in the preceding flow domain and charge distribution different than those that create a constant electrical potential everywhere on the surface of the fluid both of which could have dramatic effects on the further evolution of the jet.

In electrospinning of viscoelastic polymer solutions, the length of the initial straight part of the electrified jets is determined by the level of the longitudinal viscoelastic stresses and electric forces. However, little is known about the role of a straight segment with a non-zero initial stress which might arise from the charge distribution. On the contrary, for the free viscoelastic liquid jets rapidly propagating in air and experiencing the aerodynamically-driven bending instability, the crucial role of the initial viscoelastic stresses is well understood theoretically and their level has been measured. In particular, the method of periodic transverse vibrations was proposed which allows measurement of the level of the longitudinal stresses in uncharged jets freely moving in air, as well as an estimate of the viscoelastic relaxation time of the liquids in such jets.

In a typical electrospinning device for the manufacture of nanofibers, a steady state shape of the jet along its path is established when distance between the electrodes is kept short (not more than several centimeters). To create the jet with a steady state shape, the geometry of the orifice, the fluid pressure inside the orifice, a particular viscoelastic solution characterized by its elasticity modulus and relaxation time, a particular electrical potential distribution between the orifice and the collector is established, and any other influence on the jet are held constant. The diameter of the jet can be observed and measured as a function of the position along the path.

Figure 1:
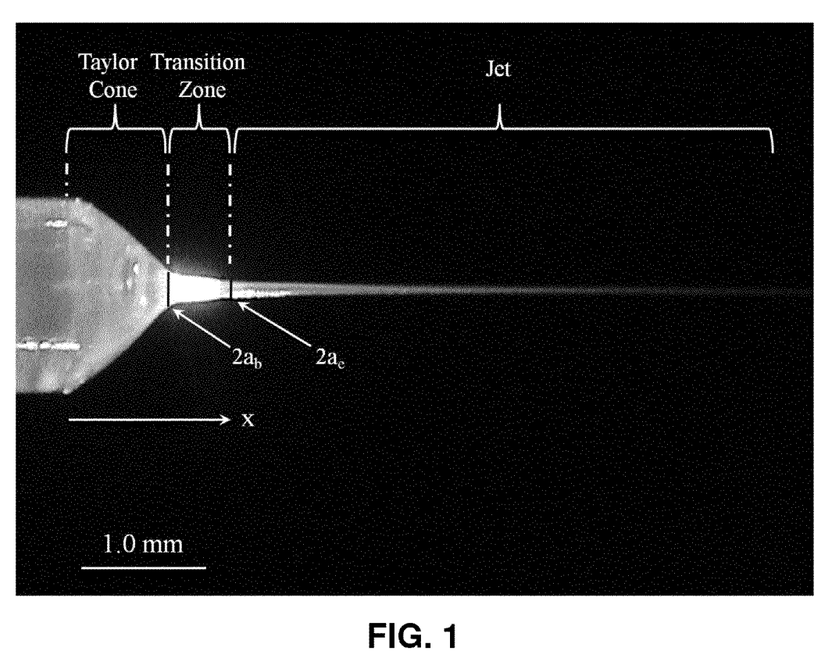
FIG. 1 is a photograph of a Taylor cone with the transition zone in an electrically-driven jet.

Stretching of polymer solutions in electrospun jets begins in the transition zone, between the Taylor cone where liquid is practically unloaded, and the beginning of the thin jet, where the liquid can already be significantly pre-stretched (see FIG. 1). As a result of this pre-stretching, the jet can possess a significant initial stress which might affect its further evolution. The rate of strain in this strong and extremely short pre-stretching process is on the order of $100 \text{ s}^{-1}$ to $1000 \text{ s}^{-1}$ and can be estimated from the results detailed in Schümmer et al., *Production of Mono-Dispersed Drops by Forced Disturbance of a Free Jet*, Ger. Chem. Eng., 5, pp. 209 to 220 (1982).

SUMMARY OF THE INVENTION

The present invention generally relates to a device for measuring characteristics of polymeric fluids (semi-dilute and concentrated polymer solutions and melts) in extremely strong elongational flows. In one embodiment, the present invention relates to a device for measuring characteristics of polymeric fluids (semi-dilute and concentrated polymer solutions and melts) in extremely strong elongational flows in spinning jets and/or electrified jets. In another embodiment, the present invention relates to a method for determining the elastic modulus and the relaxation time of a polymeric fluid. Also, the present invention enables one to determine and/or measure the primary parameters needed to describe a viscoelastic material.

In one embodiment, the present invention relates to a device for measuring various characteristics of polymeric fluids comprising: (a) at least one fluid reservoir designed to hold at least one polymeric fluid material; (b) at least one DC power supply designed to impart a DC charge to the at least one polymeric fluid material so as to cause the at least one polymeric fluid material to undergo an electrospinning and/or electrodeposition process; (c) at least one device designed to impart one or more perturbations to the at least one polymeric fluid material during the electrospinning and/or electrodeposition process; (d) at least one grounded collector designed to collect the electrospun and/or electrodeposited polymeric material; and (e) at least one device designed to observe the one or more perturbations created in the at least one polymeric fluid material.

In another embodiment, the present invention relates to a method for creating a perturbation in a polymeric fluid, the method comprising the steps of: (A) providing at least one fluid reservoir containing at least one polymeric fluid material; (B) applying at least one DC charge to the at least one polymeric fluid material in order to cause the at least one polymeric fluid material to undergo an electrospinning and/or electrodeposition process; (C) imparting one or more perturbations to the at least one polymeric fluid material during the electrospinning and/or electrodeposition process; and (D)

collecting the electrospun and/or electrodeposited polymeric material on a suitable collector.

In still another embodiment, the present invention relates to a method for producing one or more perturbations in a polymeric fluid material, the method comprising the steps of: (i) providing at least one fluid reservoir containing at least one polymeric fluid material; (ii) applying at least one DC charge to the at least one polymeric fluid material in order to cause the at least one polymeric fluid material to undergo an electrospinning and/or electrodeposition process; (iii) imparting one or more perturbations to the at least one polymeric fluid material during the electrospinning and/or electrodeposition process; (iv) collecting the electrospun and/or electrodeposited polymeric material on a suitable collector; (v) observing the one or more perturbations in the at least one polymeric fluid material during the electrospinning and/or electrodeposition process; (vi) analyzing the observations from the one or more perturbations in the at least one polymeric fluid material during the electrospinning and/or electrodeposition process; and (vii) controlling the electrospinning and/or electrodeposition process based on the data analysis of the one or more perturbations in the at least one polymeric fluid material.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIGS. 6A-C are illustrations of the propagation and widening of a single lateral displacement pulse.

FIGS. 8A and 8B are graphs of the longitudinal stress distribution over the straight unperturbed electrified jet for different applied voltages. FIG. 8A shows stress versus pulse-related time t, $\sigma_{xx}=\sigma_{xx}(t)$. while

DETAILED DESCRIPTION OF THE INVENTION

The present invention generally relates to a device for measuring characteristics of polymeric fluids (semi-dilute and concentrated polymer solutions and melts) in extremely strong elongational flows. In one embodiment, the present invention relates to a device for measuring characteristics of polymeric fluids (semi-dilute and concentrated polymer solutions and melts) in extremely strong elongational flows in spinning jets and/or electrified jets. In another embodiment, the present invention relates to a method for determining the elastic modulus and the relaxation time of a polymeric fluid. Also, the present invention enables one to determine and/or measure the primary parameters needed to describe a viscoelastic material.

In one embodiment, the present invention is directed to a measurement method based on the analysis of a single transverse pulse imposed on a jet, and its use for measurements of longitudinal viscoelastic stresses and relaxation time in the electrically-driven jets characteristic of electrospinning.

In one embodiment, the present invention relates to a device for measuring various characteristics of polymeric fluids comprising: (a) at least one fluid reservoir designed to hold at least one polymeric fluid material; (b) at least one DC power supply designed to impart a DC charge to the at least one polymeric fluid material so as to cause the at least one polymeric fluid material to undergo an electrospinning and/or electrodeposition process; (c) at least one device designed to impart one or more perturbations to the at least one polymeric fluid material during the electrospinning and/or electrodeposition process; (d) at least one grounded collector designed to collect the electrospun and/or electrodeposited polymeric material; and (e) at least one device designed to observe the one or more perturbations created in the at least one polymeric fluid material.

In another embodiment, the present invention relates to a method for creating a perturbation in a polymeric fluid, the method comprising the steps of: (A) providing at least one fluid reservoir containing at least one polymeric fluid material; (B) applying at least one DC charge to the at least one polymeric fluid material in order to cause the at least one polymeric fluid material to undergo an electrospinning and/or electrodeposition process; (C) imparting one or more perturbations to the at least one polymeric fluid material during the electrospinning and/or electrodeposition process; and (D) collecting the electrospun and/or electrodeposited polymeric material on a suitable collector.

In still another embodiment, the present invention relates to a method for producing one or more perturbations in a polymeric fluid material, the method comprising the steps of: (i) providing at least one fluid reservoir containing at least one polymeric fluid material; (ii) applying at least one DC charge to the at least one polymeric fluid material in order to cause the at least one polymeric fluid material to undergo an electrospinning and/or electrodeposition process; (iii) imparting one or more perturbations to the at least one polymeric fluid material during the electrospinning and/or electrodeposition process; (iv) collecting the electrospun and/or electrodeposited polymeric material on a suitable collector; (v) observing the one or more perturbations in the at least one polymeric fluid material during the electrospinning and/or electrodeposition process; (vi) analyzing the observations from the one or more perturbations in the at least one polymeric fluid material during the electrospinning and/or electrodeposition process; and (vii) controlling the electrospinning and/or electrodeposition process based on the data analysis of the one or more perturbations in the at least one polymeric fluid material.

In another embodiment, the present invention is a method of characterization of viscoelastic longitudinal stresses in electrospun jets of semi-dilute and concentrated polymer solutions and melts is introduced. The measured initial longitudinal stresses in the jets of about 6 weight percent aqueous solution of polyethylene oxide ($M_w$=400 kDa) are of the order of about 100 kPa, which is by two orders of magnitude larger than in any other free viscoelastic jets issued from nozzles and orifices. While not wishing to be bound to any one theory, this is believed to be attributed to elongation-driven stretching of polymeric liquids in the transition zone, between the preceding Taylor cone and the beginning of the jet, where the stretching rates are of the order of about 100 $s^{-1}$ to about 1000 $s^{-1}$. The relaxation times found are in the range of about 3 to about 8 ms, the moduli of elasticity were of the order of 100 Pa. An explanation of the reasons for the formation of the straight sections in the electrospun jets is herein discussed.

The straight sections are stabilized by the high initial longitudinal stresses in the jet generated due to strong elongation-driven stretching in the transition zone. The relaxation distance of these stresses along the jet increases with the applied voltage (which generates higher initial stresses in the transition zone) and thus the length of straight section of the jet should increase as the applied voltage increases. This indeed happens in reality. Accordingly, in one embodiment, the method of the present invention can be employed in an elongational rheometer for concentrated polymeric systems with stretching rates of the order of about 100 $s^{-1}$ to about 1000 $s^{-1}$.

In one embodiment, the present invention is directed to a method by which to measure the velocity of the fluid in the jet everywhere along the length of the jet, from the observed diameter of the jet as a function of position along the jet and the Laser Doppler Velocimeter data. The measurement of the tensile stress in the jet is done by creating a lateral displacement of a short segment near the beginning of the jet and observing the propagation of the displaced segment along the jet. This provides the information needed to measure the tensile stress as a function of position along the jet path. The combination of the observed fluid velocity data with the observed stress data at each point provides the information needed to determine the modulus of elasticity and relaxation time of polymeric liquid subjected to an extremely strong stretching. Suitable observations are made in the transition zone and the straight segment of a straight electrified jet, as defined in FIG. 1. Mathematical descriptions of the diameter of a jet along its length in terms of the many parameters involved therein have been published. Comparisons of the results from the various theoretical descriptions and experimental measurements reveal the complications and uncertainties. These uncertainties are dealt with to make calculations that predict the shape of the straight electrified jet with sufficient accuracy and to determine the viscoelastic parameters of concentrated polymer solutions and melts undergoing uniaxial elongation at extreme strain rates.

Due to the mass conservation in the transition zone (practically no solvent evaporation yet), the elongation of a material element there is $\lambda=(a_b/a_e)^2$, where $a_b$ and $a_e$ are the cross-sectional radii at the beginning and end of the transition zone. It is known to those of skill in the art that polymer solutions react to strong and almost instantaneous stretching almost as an elastic neo-Hookean (rubber-like) body with practically no relaxation involved. The stress $\sigma_{xxe}$ at the end of the transition zone (the initial stress in the jet) can then be represented by the following formula:

$$\sigma_{xxe} = 2G\lambda^2 = 2G\left(\frac{a_b}{a_e}\right)^4 \tag{1}$$

where G is the modulus of elasticity and $a_b$ and $a_e$ are measured from the photographs of the transition zone (see FIG. 1).

Figure 2:
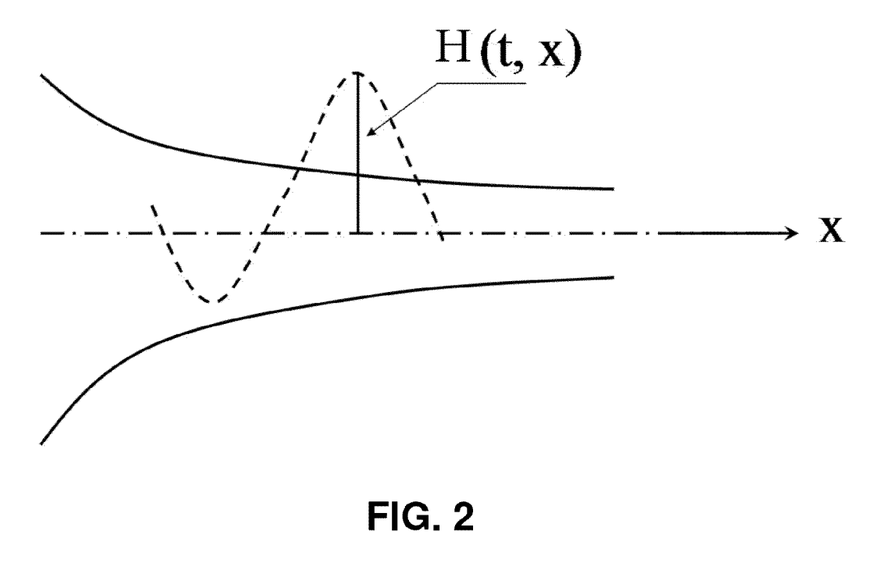
FIG. 2 is a sketch of a tapered straight jet, and lateral (bending) perturbation of its axis.

Consider now an initial straight tapering section of an electrically-driven viscoelastic jet of polymer solution moving in air. This can be a jet traveling a short inter-electrode distance of the order of 1 cm, a distance too short for a bending instability to develop, or the first part of the straight section of an electrospinning jet, preceding the loops of bending instability. The electric force acting on the jet section is longitudinal, and even if the straight section were forced to bend by an impactor, the resulting lateral electric force would still be much less than the longitudinal viscoelastic force established by the high electrical charge density in the jet cross-section and over its surface. When bending perturbations are imposed on a straight jet or its straight initial section in electrospinning, the perturbations are assumed to be sufficiently small. They are also assumed to be planar. Based on the momentumless quasi-one-dimensional equations of the dynamics of free liquid jets, it is easy to show that the normal projection of the momentum balance equation (4.19) on page 49 of Yarin et al., *Free Liquid Jets and Films: Hydrodynamics and Rheology*, Longman Scientific & Technical, Wiley & Sons, Harlow, N.Y., 1993 takes the following form:

$$\frac{\partial^2 H}{\partial t^2} + 2V(x)\frac{\partial^2 H}{\partial t \partial x} + [V(x)^2 - \sigma_{xx}(x)/\rho] = 0 \tag{2}$$

where t is time, x is the longitudinal Cartesian coordinate along the unperturbed jet axis, H=H(t,x) is the normal displacement of the jet axis (see FIG. 2), V=V(x) is an unperturbed distribution of the longitudinal liquid velocity along the jet, $\sigma_{xx}=\sigma_{xx}(x)$ is an unperturbed tensile stress in the jet cross-section, and $\rho$ is the liquid density.

In one embodiment, the present invention relies on the fact that this device utilizes electrical forces to achieve strain rates of the order of about 1000 $s^{-1}$. This can be contrasted with other devices, known in the art, for measuring elastic modulus and relaxation time of polymeric fluids that do not achieve such high strain rates. Other inventive steps are the modification of the laser Doppler instrument to also provide data characterization information about jet diameter and the taper rate of short segments of the jet, and a new type of jet excitation by a single lateral pulse.

Although the invention is explained in terms of an electrospinning process, and focuses on the characterization of fluids in electrospinning and electro-spraying, the present invention is not limited thereto. For example, the present invention is also useful for the characterization of many other kinds of fluid jets that are relevant to textile fibers (melt spinning, dry and wet spinning), scaffolds for growth of artificial organs, for biomedical uses of fibers, painting and coating, as well as hygienic and pharmacological uses of fibers and sprays.

In another embodiment, the present invention is used for characterizing polymeric fluids in the moving, electrified polymeric jet of the sort used in electrospinning. A typical segment of an electrified fluid jet elongates as it emerges from an orifice, has a decreasing cross-sectional area and ultimately solidifies into a fiber which may include less than about 10 polymer molecules in its cross-section, or may be larger in diameter than a textile fiber. The data from the measurements made by this invention are used for process development and control, for monitoring the properties of the fluid being electrospun, and for process monitoring. The parameters to be measured vary over many orders of magnitude. The fundamental purpose of the apparatus of the present invention is to determine the tensile stress acting along the axis of an element of the viscoelastic jet and its viscoelastic relaxation.

The strain rate ($\dot{\gamma}$) can be determined by measuring the cross sectional area at each end of the element and the length of the element. Stream-line flow enters the beginning end of the element, and emerges as a higher velocity, smaller diameter jet at the end of the element.

In one situation, the variation of the solvent concentration is assumed to be small along the initial section of the jet under investigation. The volumetric flow rate of the jet is assumed to be constant. The strain rate can be determined by the formulae as below:

$$Q = \pi a^2 V$$

$$V(x) = \frac{Q}{\pi a^2}$$

$$\dot{\gamma} = \frac{dV}{dx} = -\frac{2}{\pi a^3}\frac{da}{dx}$$

where a is the cross-sectional radius of the jet, V is the longitudinal velocity of the jet, Q is the volumetric flow rate, and $\dot{\gamma}$ is the elongational strain rate.

The volumetric flow rate is, in one embodiment, assumed to be conserved along a steady-state part of the jet. This procedure is satisfactory for short segments, but for longer segments the evaporation of the solvent from the jet introduces errors which can be avoided if the strain rate is determined from the jet diameter and the jet velocity measured on the same short segment of the jet. Both options are a part of the invention.

On the other hand, a laser Doppler velocimeter can be used to measure the local velocity, V(x), along the jet. Then, the strain rate can be calculated by the formula:

$$\dot{\gamma} = \frac{dV}{dx}$$

The tensile stress ($\sigma_{xx}$) is measured, for example, by creating a single lateral excursion of a short, straight element of the jet at a chosen location along the jet, by a mechanical impact or a narrow jet of air, or a solid impactor. For example, at the beginning of the jet, a brief lateral displacement of the orifice from which the jet emerges creates a useful lateral discursion of the emerging segment of the jet. Such an instantaneous displacement widens as the leading edge of the displacement propagates in the forward axial direction of the jet and the trailing edge of the displacement propagates in the backward direction (both on the background of forward flow of the unperturbed jet), so the displaced region of the jet grows wider with time. The velocity of the separation of the leading and trailing ends of the displaced region, depends on the tensile stress along the axis of the jet.

In one embodiment, the method for measuring the strain rate involves the measurement of the (constant) volumetric flow rate of the fluid. Use laser single slit diffraction patterns to measure the diameter of the jet at the beginning and end of the segment being characterized. Alternatively, optical images of the jet, at appropriate magnification may be made and the diameters determined from measurements on the image.

In one embodiment, the method for measuring the tensile stress involves the use of videography, at a lower magnification in order to obtain a suitably large field to follow the growth in the length of the laterally displaced segment, and at a frame rate that provides a suitable number of measurements of the width (length) of the displaced segment. The displacement of the midpoint of the displaced segment can also be measured from the videographic record. The density of the fluid must be known to express the tensile stress in customary units.

Stretching of polymer solutions in electrospun jets begins in the transition zone between the Taylor cone where liquid is practically unloaded and the beginning of the thin jet, where it can already be significantly pre-stretched (see FIG. 1). As a result of this pre-stretching the jet can inherit a significant longitudinal elastic stress which might affect its further evolution. A strong and extremely short stretching with the stretching rates of the order of about $100\ \text{s}^{-1}$ to about $1000\ \text{s}^{-1}$ in this zone can be estimated from the results detailed in Yarin et al., *Free Liquid Jets and Films: Hydrodynamics and Rheology*, Longman Scientific & Technical, Wiley & Sons, Harlow, N.Y., 1993, and will be measured. It is known by those of skill in the art that polymer solutions react to strong and almost instantaneous stretching almost as an elastic neo-Hookean (rubber-like) body with no relaxation involved. Due to the mass conservation in the transition zone (practically no evaporation yet), the elongation of a material element there $\lambda = (a_b/a_e)^2$ where $a_b$ and $a_e$ are the jet cross-sectional radii at the beginning and end of the transition zone. The inherited stress $\sigma_{xxe}$ at the end of the transition zone is then be represented by the following formula:

$$\sigma_{xxe} = 2G\lambda^2 = 2G\left(\frac{a_b}{a_e}\right)^4 \tag{1}$$

where G is the modulus of elasticity and $a_b$ and $a_e$ are measured from the photographs of the transition zone.

Consider now an initial straight tapering section of an electrically-driven viscoelastic jet of polymer solution moving in air. This may be a jet traveling a short inter-electrode distance of the order of 1 cm, when bending instability cannot be developed, or a first straight section of an electrospun jet at a larger inter-electrode distance preceding the loops resulting from the bending instability. The electric force acting on the jet section is longitudinal, and even if the straight section would be forced to bend, the arising lateral electric force would still be much less than the longitudinal viscoelastic force in the jet cross-section. When bending perturbations are imposed on a straight jet or its straight initial section in electrospinning, the perturbations are assumed to be sufficiently small. They are also assumed to be planar. Based on the momentumless quasi-one-dimensional equations of the dynamics of free liquid jets, it can be shown that the normal projection of the momentum balance equation (4.19) on page 49 of Yarin et al., *Free Liquid Jets and Films: Hydrodynamics and Rheology*, Longman Scientific & Technical, Wiley & Sons, Harlow, N.Y., 1993 takes the following form:

$$\frac{\partial^2 H}{\partial t^2} + 2V(x)\frac{\partial^2 H}{\partial t \partial x} + [V(x)^2 - \sigma_{xx}(x)/\rho] = 0 \tag{2}$$

where t is time, x is the longitudinal Cartesian coordinate along the unperturbed jet axis, H=H(t,x) is the normal displacement of the jet axis (see FIG. 2), V=V(x) is an unperturbed distribution of the longitudinal liquid velocity along the jet, $\sigma_{xx}=\sigma_{xx}(x)$ is an unperturbed tensile stress in the jet cross-section, and $\rho$ is the liquid density.

The hyperbolic Equation (2) describes propagation of sufficiently small bending perturbations along a straight tapering viscoelastic jet. It is also derived as Equation (2) in Goren et al., *Transverse Wave Motion on a Thin Capillary Jet of a Viscoelastic Liquid*, Phys. Fluids 1961; 4, pp. 575 to 579. However, its general solution relevant for pulse propagation is not considered there or in the other related works. Note, that the normal (lateral) velocity of the jet related to bending perturbations is given by $V_n = \partial H/\partial t$.

The hyperbolic Equation (2) possesses two characteristics:

$$\xi(t, x) = \int_0^x \frac{dx}{V + \sqrt{\sigma_{xx}/\rho}} - t = C_1 \qquad (3)$$

$$\eta(t, x) = \int_0^x \frac{dx}{V - \sqrt{\sigma_{xx}/\rho}} - t = C_2 \qquad (4)$$

where $C_1$ and $C_2$ are constants. Therefore, the general solution of Equation (2) is given by:

$$H(t, x) = \Phi\left[\int_0^x \frac{dx}{V + \sqrt{\sigma_{xx}/\rho}} - t\right] + F\left[\int_0^x \frac{dx}{V - \sqrt{\sigma_{xx}/\rho}} - t\right] \qquad (5)$$

where $\phi=\phi(\bullet)$ and $F=F(\bullet)$ are arbitrary functions. For any particular perturbation pattern (e.g., time-periodic perturbations or a single pulse) these functions can be always found via the initial conditions, namely:

$$H = H_0(x) \text{ at } t = 0; V_n = \frac{\partial H}{\partial t} = V_{n0}(x) \text{ at } t = 0 \qquad (6)$$

where the initial wave pattern $H_0(x)$ and the lateral velocity distribution related to it $V_{n0}(x)$ can be, in principle, measured experimentally. The longitudinal velocity distribution in the unperturbed jet is also known in principle as $V(x)=Q/[\pi a(x)^2]$, where Q is the volumetric flow rate and the cross-sectional radius distribution $a=a(x)$ can be measured experimentally or calculated using the existing theoretical models. The unperturbed tensile stress distribution $\sigma_{xx}(x)$ along the jet is not immediately measurable, and our aim is to establish it using the above results.

Determination of $\sigma_{xx}(x)$ does not require knowledge of $V(x)$ (or $a(x)$) and $V_{n0}(x)$. The solution (5) represents a superposition of two d'Alembert waves (signals) $\phi$ and F, which propagate with speeds $V+\sqrt{\sigma_{xx}/\rho}$ and $V-\sqrt{\sigma_{xx}/\rho}$, respectively. Any pulse-like perturbation widens by $2\sqrt{\sigma_{xx}/\rho}\Delta t$ during time $\Delta t$, since it is propagated by the two signals. If a lateral perturbation pulse would be applied to the jet axis at a certain coordinate x, and the width of its profile at $t=\Delta t$ and $t=0$ (the pulse application moment) would be recorded and compared, then a widening W can be measured. Then, $$\sigma_{xx} = \rho\left(\frac{W}{2\Delta t}\right)^2 \qquad (7)$$

Repeating the experiment with the pulse being applied at different coordinates x, one can measure the whole profile of the unperturbed stress $\sigma_{xx}(x)$ along the jet. If the duration of the pulse observation time $\Delta t$ is taken much less than the shortest expected relaxation time (say, $\Delta t$ is taken of the order of 0.5 ms), one can avoid multiple pulse application at different locations x. In the latter case observing one pulse propagating over the whole jet, we can consider it as different pulses applied at different locations, while the local observation time $\Delta t$ is taken that short that the elastic relaxation time characteristic of stress a in the material element observed will be longer than the observation period from t to t+$\Delta t$. Then, the measured value of $\sigma_{xx}$ could be attributed to the location of the pulse peak between t and t+$\Delta t$. On the other hand, the measured dependence of $\sigma_{xx}$ on time t which comprises all the results for pulse locations at different time moments t will, in fact, correspond to the stress relaxation in a material element of fluid as it travels down the jet.

The hyperbolic Equation (2) describes propagation of sufficiently small bending perturbations along a straight tapering viscoelastic jet it is also derived as Equation (2) in Goren et al., *Transverse Wave Motion on a Thin Capillary Jet of a Viscoelastic Liquid*, Phys. Fluids 1961; 4, pp. 575 to 579. However, its general solution relevant for pulse propagation was not considered there or in the other related works. Note, that the normal (lateral) velocity of the jet related to bending perturbations is given by $V_n = \partial H/\partial t$.

The hyperbolic Equation (2) possesses two characteristics:

$$\xi(t, x) = \int_0^x \frac{dx}{V + \sqrt{\sigma_{xx}/\rho}} - t = C_1 \qquad (3)$$

$$\eta(t, x) = \int_0^x \frac{dx}{V - \sqrt{\sigma_{xx}/\rho}} - t = C_2 \qquad (4)$$

where $C_1$ and $C_2$ are constants. Therefore, the general solution of Equation (2) is given by:

$$H(t, x) = \Phi\left[\int_0^x \frac{dx}{V + \sqrt{\sigma_{xx}/\rho}} - t\right] + F\left[\int_0^x \frac{dx}{V - \sqrt{\sigma_{xx}/\rho}} - t\right] \qquad (5)$$

where $\phi=\phi(\bullet)$ and $F=F(\bullet)$ are arbitrary functions. For any particular perturbation pattern (e.g., time-periodic perturbations or a single pulse) these functions can be always found via the initial conditions, namely:

$$H = H_0(x) \text{ at } t = 0; V_n = \frac{\partial H}{\partial t} = V_{n0}(x) \text{ at } t = 0 \qquad (6)$$

where the initial wave pattern $H_0(x)$ and the lateral velocity distribution related to it $V_{n0}(x)$ can be, in principle, measured experimentally. The longitudinal velocity distribution in the unperturbed jet is also known in principle as $V(x)=Q/[\pi a(x)^2]$, where Q is the volumetric flow rate and the cross-sectional radius distribution $a=a(x)$ can be measured experimentally or calculated using the existing theoretical models. The unperturbed tensile stress distribution $\sigma_{xx}(x)$ along the jet is not immediately measurable, and our aim is to establish it using the above results.

Determination of $\sigma_{xx}(x)$ does not require knowledge of $V(x)$ (or $a(x)$) and $V_{n0}(x)$. The solution (5) represents a superposition of two d'Alembert waves (signals) $\phi$ and F, which propagate with speeds $V+\sqrt{\sigma_{xx}/\rho}$ and $V-\sqrt{\sigma_{xx}/\rho}$, respectively. Any pulse-like perturbation widens by $2\sqrt{\sigma_{xx}/\rho}\Delta t$ during time Δt, since it is propagated by the two signals. The widening of the pulse W between t=0 and t=Δt can be measured. Then, $$\sigma_{xx} = \rho \left( \frac{W}{2\Delta t} \right)^2 \quad (7)$$

(i): Repeating the experiment with the pulse being applied at different coordinates x, one can, in principle, measure the whole profile of the unperturbed stress $\sigma_{xx}(x)$ along the jet. (ii): If the duration of the pulse observation time Δt is taken much less than the shortest expected relaxation time (say, Δt is taken of the order of 0.5 ms), one can avoid multiple pulse application at different locations x. In the latter case observing a single pulse propagating along the whole jet, we can consider it as different pulses applied at different locations, while the local observation time Δt is taken that short that the elastic relaxation time characteristic of stress $\sigma_{xx}$ in an observed jet segment will be longer than the observation period from t to t+Δt. Then, the measured value of W and thus $\sigma_{xx}$ could be attributed to the location of the pulse peak between t and t+Δt. The experimental procedure based on observations of a single pulse (ii) was implemented in the present work.

EXAMPLES

Polyethylene oxide, PEO, ($M_w$=400 kDa), purchased from Scientific Polymer Products, Inc., is used as a 6 weight percent solution in water. The density of the solution is $10^3$ kg/m$^3$, zero shear viscosity 5 Pa·s, surface tension 61 mN/m, and the electrical conductivity 0.0125 S/m. The experiments are done under ambient conditions at room temperature and relative humidity of about 25%.

Figure 3:
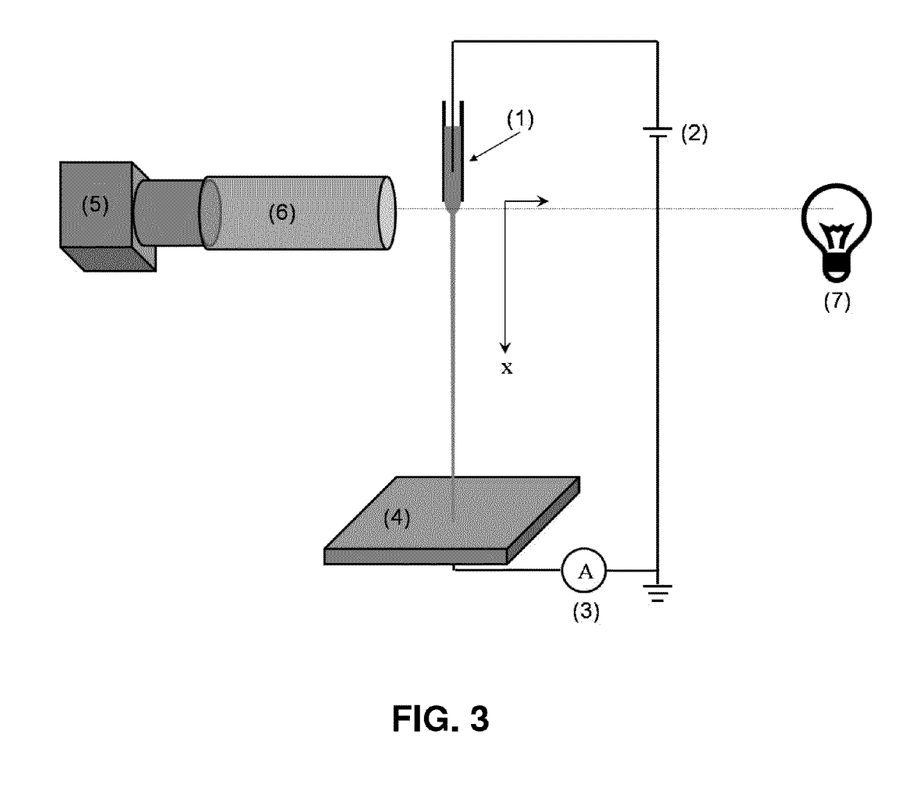
FIG. 3 is a schematic drawing of the experimental setup for measuring radius and velocity distributions and evaluating the stretching rate.

A digital video camera attached to an optical microscope is used to record the profile of the transition zone between the Taylor cone and the beginning of the jet (see FIG. 3). The experiment is conducted as follows. Polymer solutions are held in a glass pipette which had tip several centimeters long with an 800 μm inner diameter. A copper wire is immersed in the solution and connected with a high voltage power supply which could generate DC voltage up to about 13 kV. In another embodiment, the DC voltage can be in the range from about 1 kV to about 100 kV, or from about 3 kV to about 80 kV, or even 5 kV to about 60 kV. Her, as well as elsewhere in the specification and claims, individual range values can be combined to form additional non-disclosed ranges. A grounded horizontal plate is placed below the pipette tip to serve as a collector-electrode. The distance between the pipette tip and the grounded plate can be adjusted from 0.1 to 30 cm. An ammeter is connected between the collector plate and ground to measure the current carried by the electrically-driven jet.

FIG. 3 shows a schematic drawing of the experimental setup for measuring radius and velocity distributions and evaluating the stretching rate. In FIG. 3, the following reference numerals represent the following items: (1) Pipette; (2) high voltage DC power supply; (3) ammeter; (4) grounded collector; (5) digital video camera; (6) optical microscopy; and (7) illumination light.

Figure 4A:
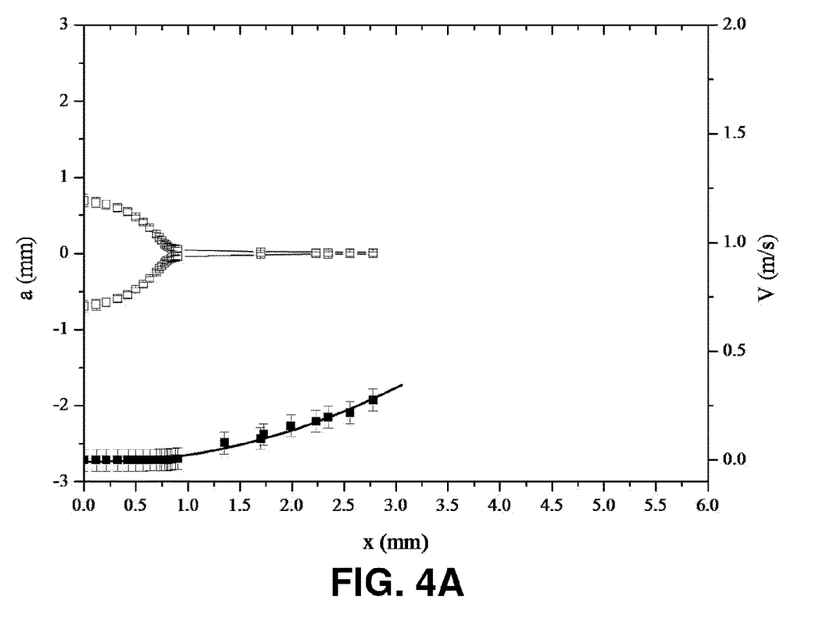
FIGS. 4A-C are graphs of the profile of the transition zone following the Taylor cone and the beginning of the jet as well as the velocity distribution, as measured for the applied voltage of 3 kV (4A); 4 kV (4B); and 5 kV (4C)
Figure 4B:
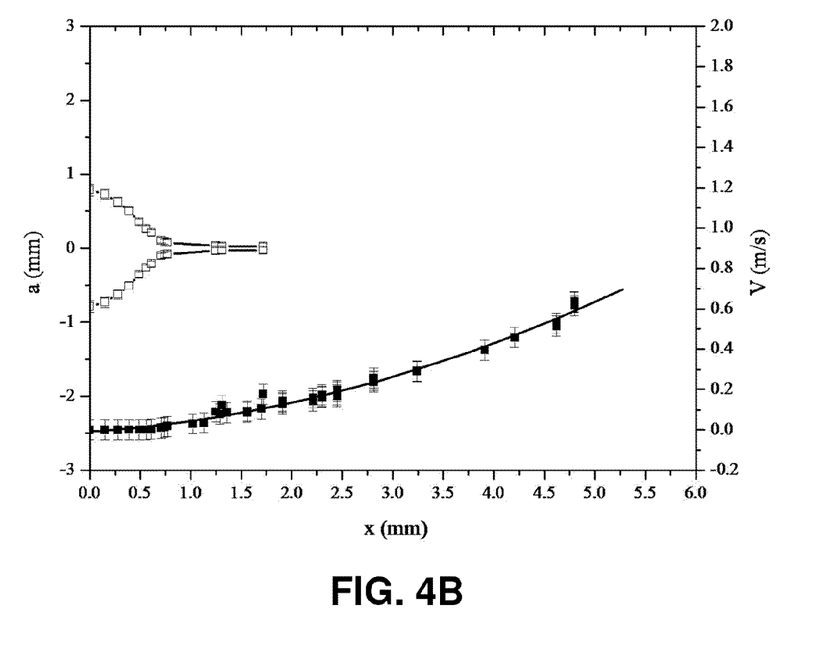
Figure 4C:
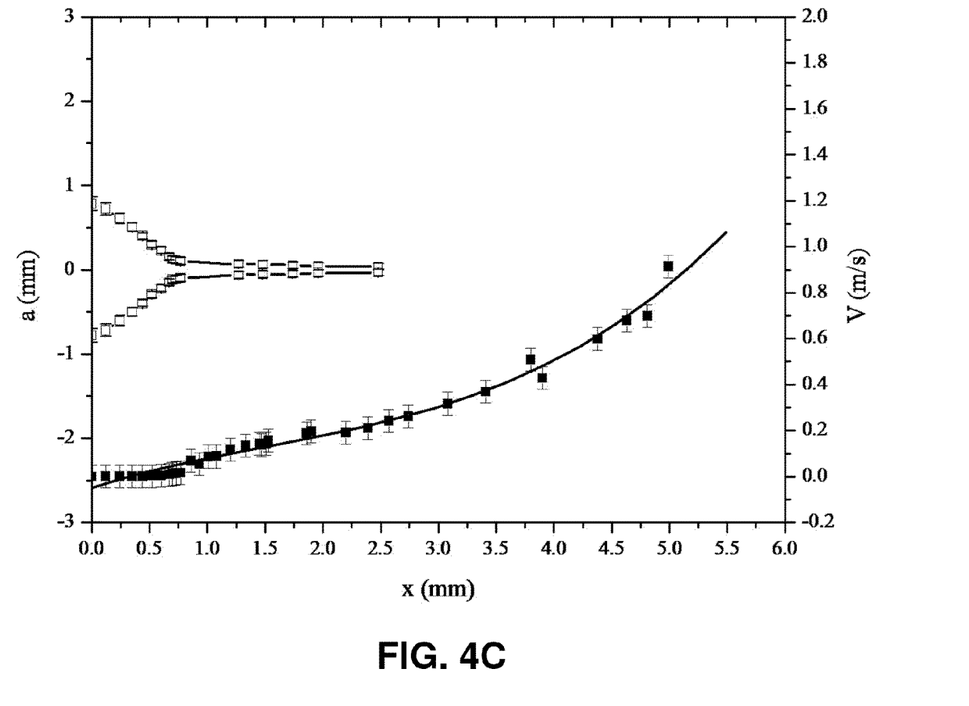

The cross-sectional radius in the transition zone a=a(x) is measured from the images of the transition zone (FIG. 4). Then, the longitudinal velocity V=V(x) is calculated as V=Q/($\pi a^2$) where Q is the volumetric flow rate sustained in the experiment. A Laser Doppler Velocimeter is used to measure the velocity of the jet following the transition zone. The velocity profiles in the transition zone and the jet are combined and matched each other smoothly (FIG. 4).

FIG. 4 shows a profile of the transitional zone following the Taylor cone and the beginning of the jet. The cross-sectional radius is shown as a=a(x) (the symmetric profile in the middle-left), where the axial coordinate x is rendered from the first observable cross-section of the drop. At the end of the transition zone and the beginning of the jet, x=$x_e$. The velocity distribution measured is shown by the solid curve below the profile a=a(x). The change in the jet diameter after the transition zone is practically unseen in this scale which is the reason that the velocity distribution in the Figure in two cases extends beyond the profile of the transition zone. Measured for the applied voltage of 3 kV (4A); 4 kV (4B); and 5 kV (4C).

Figure 5:
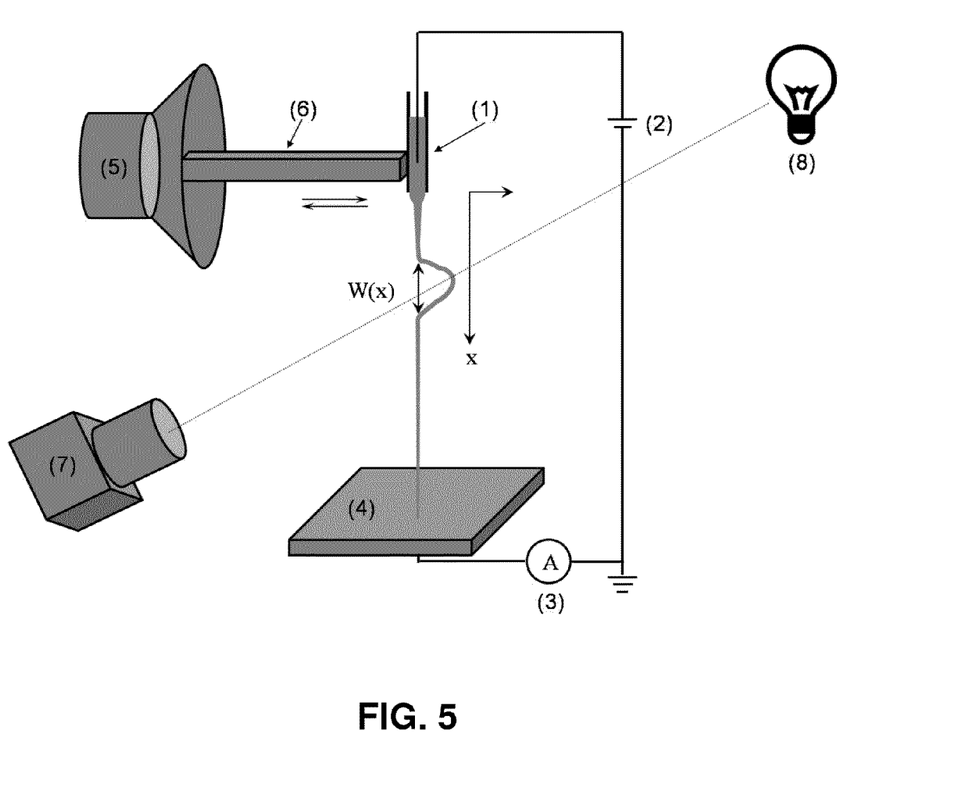
FIG. 5 is a schematic drawing of the experimental setup for measuring longitudinal stresses in jets.

The single-pulse experiment is conducted as follows. A polystyrene bar with a high stiffness and low density is glued onto a loudspeaker which produced a single displacement pulse when a suitable electrical pulse is applied. The polystyrene bar is positioned as shown in FIG. 5, so that the displacement pulse from the loudspeaker imparted a pulse-like lateral motion to the tip of the pipette. The amplitude of the lateral motion of the jet is about 2 mm. The time from the beginning to the end of the pulse is about 4 to 5 ms. As a result of the tip motion, a lateral displacement is imposed on the jet.

FIG. 5 is a schematic drawing of the experimental setup for measuring longitudinal stresses in jets where the following reference numerals represent the following items: (1) Pipette; (2) high voltage DC power supply; (3) ammeter; (4) grounded collector; (5) loudspeaker; (6) polystyrene bar; (7) high speed camera; and (8) illumination light.

The stretching rate in the transition zone is equal to dV/dx. Its values are found using the data depicted in FIG. 4 and are in the range about 100 s$^{-1}$ to about 1000 s$^{-1}$. This is a tremendously high rate of strain for 6% polymer solutions which could be hardly achieved in any other experiment.

Figure 6A:
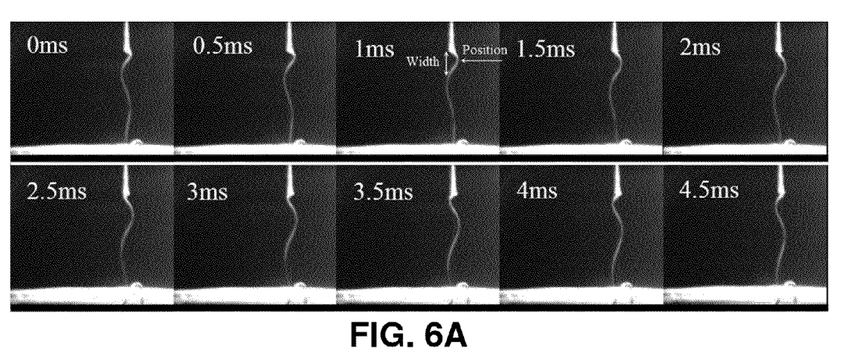
FIG. 6A illustrates an inter-electrode distance L=5.5 cm, potential difference of U=3 kV, and the electric current I=100 nA.
Figure 6B:
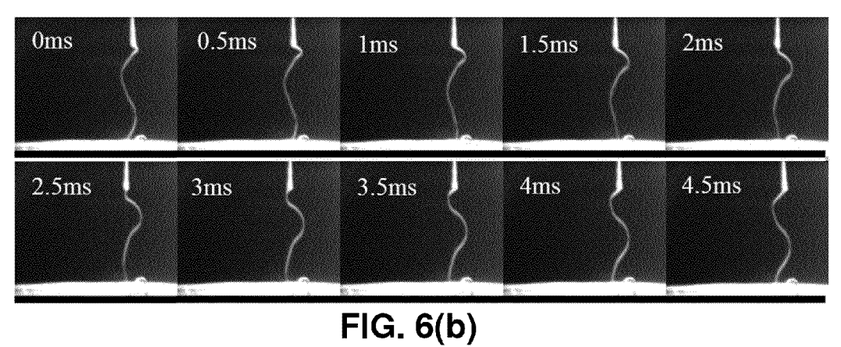
FIG. 6B illustrates an inter-electrode distance L=5.5 cm, potential difference of U=4 kV, and the electric current I=390 nA.
Figure 6C:
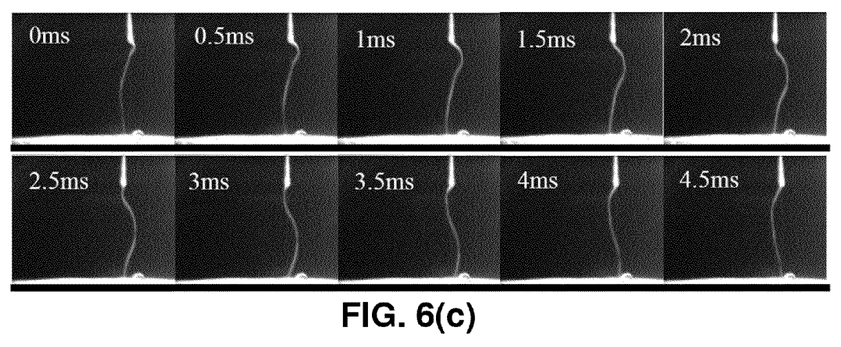
FIG. 6C illustrates an inter-electrode distance L=5.5 cm, potential difference of U=5 kV, and the electric current I=880 nA. In all the cases the jet is straight before the lateral displacement pulse is applied.
Figure 7:
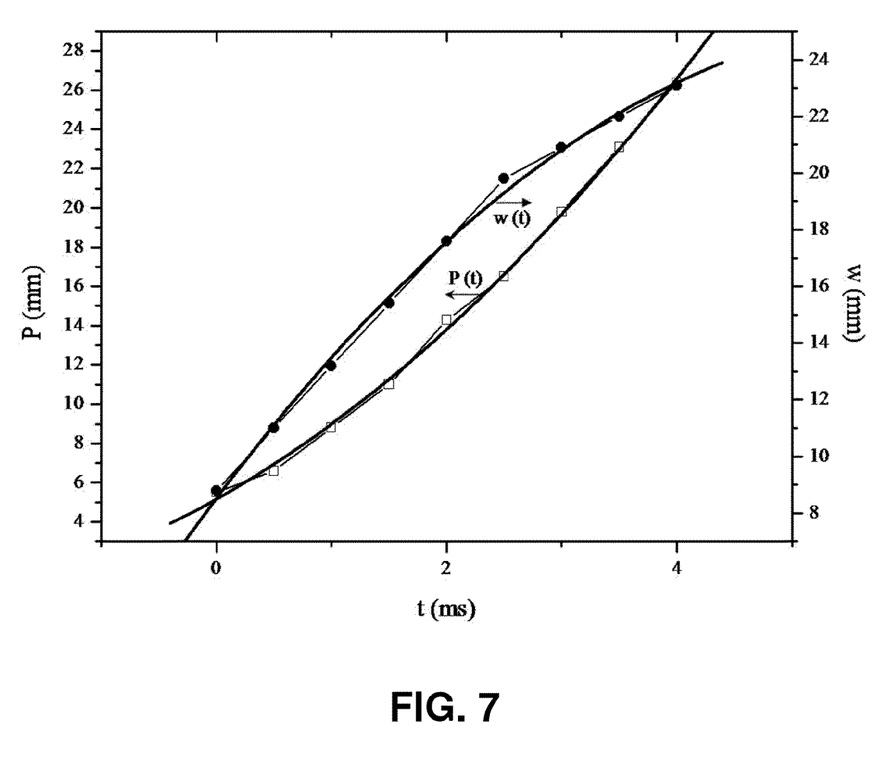
FIG. 7 is a graph of the pulse peak location and width versus time.

The pulse propagation and widening images are presented in FIG. 6 for the applied voltage pulling the jet to the grounded electrode in the range from about 3 to about 5 kV. The images in FIG. 6 are measured to determine the location of the pulse peak, P, and the width, w, versus time. Peaks observations and measurements are done at sufficiently short time intervals. The observations of a single peak propagating over the jet are used to acquire information for the entire length of the jet. An example of such processing is shown in FIG. 7. Data for w(t) is approximated by a smooth function shown in FIG. 7 as a solid line. It is possible to differentiate w(t) and find the derivative ∂w/∂t corresponding to any instantaneous location of the lateral displacement pulse propagating over the whole jet. The data in FIG. 7 is used to calculate the widening rate of the pulse at different locations along the jet. It is possible to calculate the pulse widening over time intervals (e.g., Δt→0), much shorter than any expected relaxation time value. Using W/Δt=∂w/∂t the stress $\sigma_{xx}$ in the unperturbed jet is calculated via Equation (7).

FIG. 6 illustrates the propagation and widening of a single lateral displacement pulse. FIG. 6A illustrates an inter-electrode distance L=5.5 cm, potential difference of U=3 kV, and the electric current I=100 nA. FIG. 6B illustrates an inter-electrode distance L=5.5 cm, potential difference of U=4 kV, and the electric current I=390 nA. FIG. 6C illustrates an inter-electrode distance L=5.5 cm, potential difference of U=5 kV, and the electric current I=880 nA. In all the cases the jet is straight before the lateral displacement pulse is applied.

FIG. 7 is a plot illustrating pulse peak location P and width w versus time. The broken lines connect the data points shown by symbols, the smoothed lines show the best fit of the data. The width-time curve is used to find ∂w/∂t=W/Δt needed to calculate the longitudinal stress $\sigma_{xx}$ in the unperturbed jet using Equation (7). The voltage applied to issue the jet is 3 kV in this case.

Figure 8A:
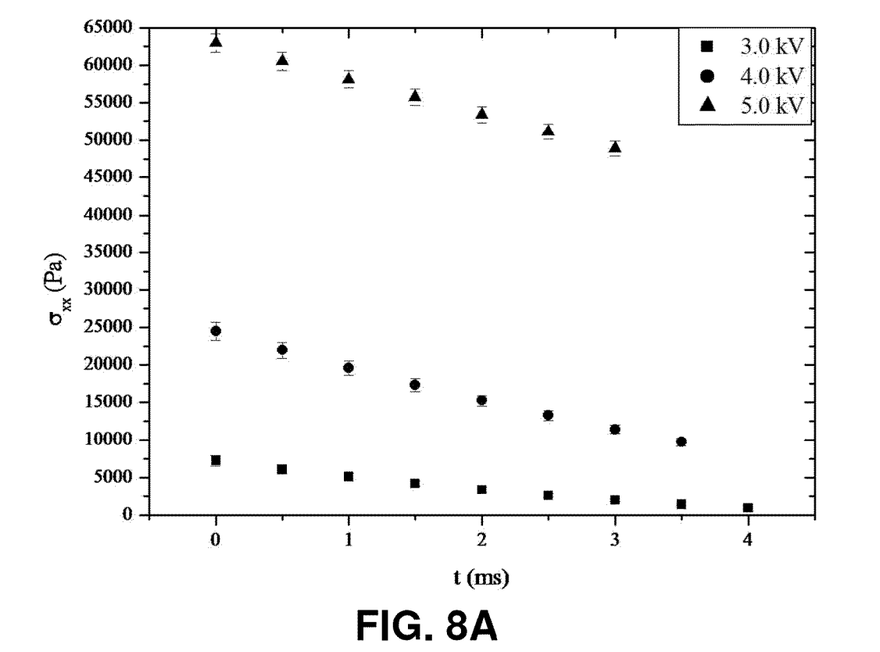
Figure 8B:
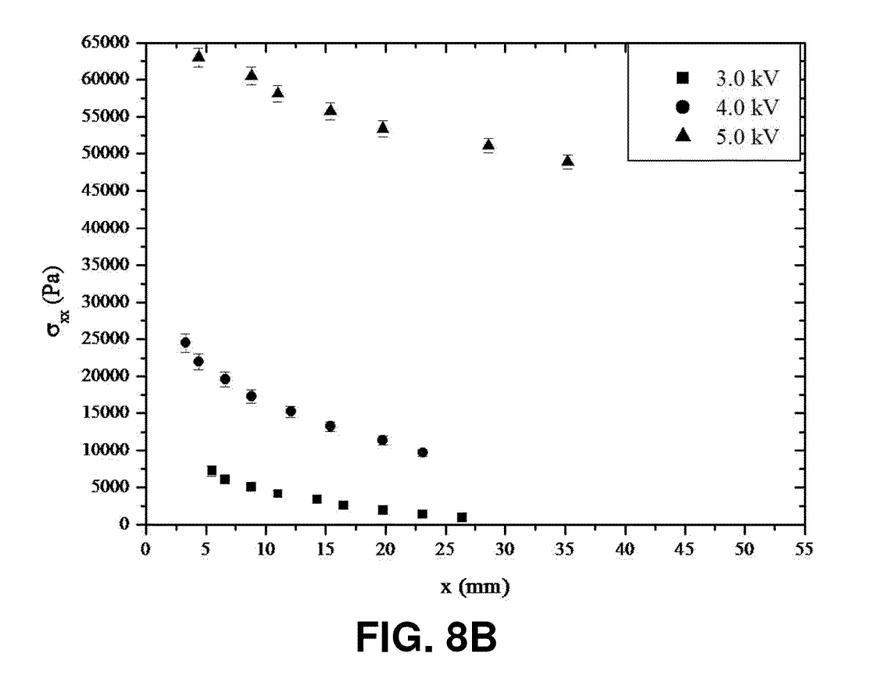
FIG. 8B shows the Eulerian presentation as $\sigma_{xx}=\sigma_{xx}(x)$.

The value of $\sigma_{xx}$ thus found can be associated with the value of t used to calculate the derivative ∂w/∂t=W/Δt or the corresponding peak location P=P(t)=x. Thus, $\sigma_{xx}=\sigma_{xx}(t)$ can be recast into $\sigma_{xx}=\sigma_{xx}(x)$. These distributions are presented in FIG. 8.

Figure 9:
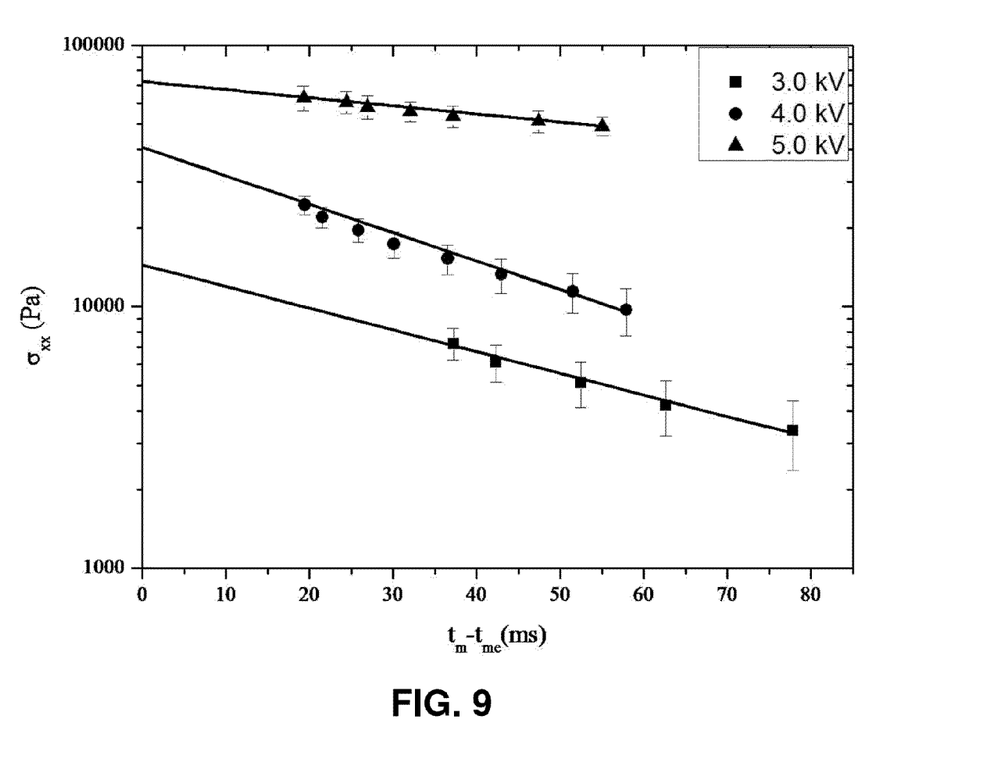
FIG. 9 is a graph of the Larangian presentation of $\sigma_{xx}=\sigma_{xx}(t_m-t_{me})$.

For a material element of the jet to reach a location x, it takes a different time $t_m$ than for a pulse t (the latter moves over the liquid jet). For a material element it takes time $$t_m = \int_0^x \frac{dx}{V(x)} \tag{8}$$

to reach x. Then, the stress distribution $\sigma_{xx}(x)$ (in the Eulerian sense) can be recast into $\sigma_{xx}(t_m)$ (in the Lagrangian sense), as shown in FIG. 9.

The initial stresses at the beginning of the jets generated because of the pre-stretching in the transition zone at the end of the Taylor cone appeared to be of the order of about 10 to about 100 kPa (see FIGS. 8 and 9). The latter value is larger than those reported for the uncharged jets by two orders of magnitude. This reveals the strong electrical forces affecting polymer solutions in the transition zone prior they form a jet. The higher the applied voltage is (at a fixed inter-electrode distance), the higher is the value of the initial longitudinal stress generated in the jets. FIGS. 8 and 9 show that relaxation effects in the straight part of the electrospun jets dominate the stretching effect of the electric stresses acting on them (which means that the flow is weak there, following the terminology used in polymer physics). Therefore, the longitudinal stresses relax along the jet. This result, in fact, invalidates all the theoretical models of the straight part of the viscoelastic electrospun jets published so far, since they disregard the existence of these high initial longitudinal stresses generated in the transition zone between the Taylor cone and the beginning of the jet. Moreover, the results in Bazilevsky et al., *Orientational Effects in Capillary Breakup of Jets and Threads of Dilute Polymer Solutions*, Sov. Phys. Dokl., 257, pp. 336 to 339 (1981) (English version in Vol. 26) (in particular, in FIG. 3.25 on p. 141) shows that growth of bending perturbations is delayed by initial high longitudinal stresses in the pre-stretched jets.

Even though this result is found in Bazilevsky et al. for the aerodynamically-driven bending instability, it can be immediately recast for the electrically-driven bending instability, since the equivalence of the two phenomena is established. This equivalence allows the following interpretation of the results presented in FIGS. 8 and 9—the electrically-driven bending instability is impossible from the tip of the Taylor cone up to the distance of about 2 to about 4 cm from it, because there the stabilizing longitudinal stresses are sufficiently high. This indeed happens in reality. Moreover, the results depicted in FIGS. 8 and 9 suggest that the straight section of an electrospun jet should be longer if the jet is formed at a higher applied voltage. Again, the predicted increase in the length of the straight segment of the jet with an increase in the applied voltage is seen in experiments.

FIG. 8 shows the longitudinal stress distribution over the straight unperturbed electrified jet for different applied voltages. The inter-electrode distance is held at 5.5 cm. Specifically, FIG. 8A shows stress versus pulse-related time t, $\sigma_{xx}=\sigma_{xx}(t)$. while FIG. 8B shows the Eulerian presentation as $\sigma_{xx}=\sigma_{xx}(x)$. The symbols show the experimental data for different applied voltages.

FIG. 9 is a graph illustrating the Lagrangian presentation $\sigma_{xx}=\sigma_{xx}(t_m-t_{me})$. The time moments when the material element exits the transition zone and reaches the beginning of the jet is denoted by $t_{me}$. The values of $t_{me}$ are 15145 ms, 1880 ms and 1183 ms for the voltages of 3 kV, 4 kV and 5 kV, respectively. The distributions of stress $\sigma_{xx}$ versus $t_m-t_{me}$ are plotted in semi-logarithmic scale. The symbols show the experimental data for different applied voltages; lines are plotted using Equations (9) and (10).

The initial longitudinal stress $\sigma_{xxe}$ should be attributed to $t_m-t_{me}=0$ in each experiment depicted in FIG. 9. The values of $t_{me}$ for these experiments are listed in the caption to FIG. 9. It is emphasized that these values incorporate all the prehistory of the fluid particles when they moved from the very bottom of the Taylor cone where the flow is extremely slow and the residence time is large. That is the reason that the values of $t_{me}$ (and $t_m$) are of the order of $10^3$-$10^4$ ms. Then, fitting of Equation (1) (with $a_b$ and $a_e$ being measured from the images similar to that in FIG. 1) reveals the corresponding values of the modulus of elasticity G. It is found that G=53.26 Pa, 163.3 Pa and 395.4 Pa for the applied voltages U=3.0 kV, 4.0 kV and 5.0 kV, respectively.

Stress relaxation in a material liquid element moving along the jet seen in FIG. 9 can be interpreted using the expression derived via the integration of the equations of the Upper-Convected Maxwell model (UCM) with a single relaxation time $$\sigma_{xx} = \sigma_{xxe}\exp[-(t_m - t_{me})/\theta_{eff}] \tag{9}$$

$$\theta = \frac{\theta_{eff}}{1 + 2\left(\frac{dV}{dx}\right)_{max}\theta_{eff}} \tag{10}$$

where $\theta_{eff}$ is the effective relaxation time; θ is the real relaxation time corresponding to contraction of macromolecules to their equilibrium length (the Rouse relaxation process); $(dV/dX)_{max}$ is taken as the largest (positive) value of the stretching rate. Fitting Equations (9) and (10) to the experimental data in FIG. 9, one can find $\sigma_{xxe}$ and A (shown in Table 1). Therefore, both characteristic rheological parameters of polymer solutions G and θ can be established in one experiment. The initial elongational viscosity in the jet is then estimated as $\mu=\sigma_{xxe}\theta$ (Table 1).

Equations (9) and (10) follow from the integration of the following rheological constitutive equations of the UCM model $$\frac{d\tau_{xx}}{dt_m} = \left(2\frac{dV}{dx} - \frac{1}{\theta}\right)\tau_{xx} + 2\frac{\mu}{\theta}\frac{dV}{dx} \tag{11}$$

$$\frac{d\tau_{yy}}{dt_m} = -\left(\frac{dV}{dx} + \frac{1}{\theta}\right)\tau_{yy} - \frac{\mu}{\theta}\frac{dV}{dx} \tag{12}$$

valid for uniaxial elongation in a jet, where $\tau_{xx}$ and $\tau_{yy}$ are the longitudinal and lateral deviatoric stresses in the jet, while the longitudinal stress $\sigma_{xx}=\tau_{xx}-\tau_{yy}$. The initial conditions are: $t=t_{me}$, $\tau_{xx}=\tau_{xxe}$, $\tau_{yy}=\tau_{yye}$ (and thus $\sigma_n=\sigma_{xxe}=\tau_{xxe}-\tau_{yye}$). The integration leading to Equations (9) and (10) is done for $dV/dx=(dV/dx)_{max}$=const. The result shows (as expected in jets) that $\tau_{xx} \gg \tau_{yy}$, and thus $\sigma_{xx} \approx \sigma_{xx} \approx \sigma_{xxe}\exp\{-[1/\theta-2(dV/$ dx)$_{max}$]($t_m$−$t_{me}$)}. The fact that the experimental data show that the stress $\sigma_{xx}$ decreases when a material element moves along the jet, means that in the present case the viscoelastic relaxation reduces the tensile stress faster than the elongation due to the electric field increases the stress, and thus 1/θ>2 (dV/dx)$_{max}$. In this sense, the flow in the straight part of the jet is weak, whereas the flow in the preceding transition zone is strong (since it results in a build-up of the longitudinal stress). It is emphasized that Equations (9) and (10) account for the jet stretching by the electric field which determines the value of (dV/dx)$_{max}$. In a more detailed analysis, the integration of Equations (11) and (12) could be conducted with accounting for the fact that dV/dx could vary along the jet. The latter is described in the framework of a conjugate problem incorporating the quasi-one-dimensional equations of the mass and momentum balance for jets, the rheological constitutive Equations (11) and (12) and the electric field description accounting for the interaction of the surface charges on the jet with the imposed electric field.

Examples of numerical solutions of similar conjugate problems could be found in Bazilevsky et al., *Breakup of an Oldroyd Liquid Bridge as a Method for Testing the Rheological Properties of Polymer Solutions*, Polym. Sci. Ser. A, 43, pp. 716 to 726 (2001), and Bazilevsky et al., *The First Experience of Application of Rheotester Device in Biorheology*, Biorheology, 29, p. 157 (1992) (without accounting for the initial stresses). The present work avoids dealing with the conjugate problem and detailed calculation of the electric field about the jet, because the present invention uses the experimental data for V(x) to evaluate dV/dx. Since the experimental data obviously reflect the effects of the electric field via V(x), the parameter values obtained and presented in Table 1 are affected by the electric field properly, even though there was no need to calculate it.

It is worth noting that electrospun jets consist of four distinct zones: Taylor cone (a very weak, almost Newtonian flow), transition zone (a strong elongational flow at rates of about 100 s$^{-1}$ to about 1000 s$^{-1}$), straight part (a weak elongational flow at a strain rate averaged above the entire length of the straight segment that is of the order of about 20 s$^{-1}$), and bending loops (with an initial strong elongational flow with strain rates of the order of about 1000 s$^{-1}$ which decreases rapidly with length).

Stretching in the transition zone is very strong (at the rates of about 100 s$^{-1}$ about 1000 s$^{-1}$). Therefore, the method outlined here can be used for the elongational rheometry of concentrated polymer solutions and melts under the conditions of an extremely strong elongation.

TABLE 1

| U(kV) | $\sigma_{xxe}$(Pa) | G (Pa) | θ (ms) | μ (Pa · s) |
|---|---|---|---|---|
| 3.0 | 14431.0 | 53.26 | 8.27 | 119.3 |
| 4.0 | 26455.8 | 163.3 | 3.04 | 80.4 |
| 5.0 | 64050.3 | 395.4 | 2.97 | 190.2 |

Table 1, above, details the characteristics of polyethylene oxide solutions calculated from Equations (9) and (10).

In one embodiment, the present invention relates to the measurement of viscoelastic longitudinal stresses in straight electrically-driven jets of polymer solutions is proposed and applied to the cases characteristic of electrospinning. In one embodiment, the method is based on the observation of propagation of a single lateral pulse imposed on the jet and of the profile of the unperturbed jet. The results revealed that the initial longitudinal stress created by the electric stretching of the jet as it transforms from the Taylor cone is of the order of about 10 kPa to about 100 kPa. These values are by one or two orders of magnitude larger than those measured for uncharged viscoelastic jets. This shows that stretching of polymer solutions in the transition zone of the electrically-driven jets following the Taylor cone is very strong (the rates of stretching are of the order of about 100 s$^{-1}$ to about 1000 s$^{-1}$). This elucidates the real physical pattern responsible for the formation of the straight part of the electrospinning jets. The liquid stretching by the electrical field in the straight part of the jet weakens, as the jet elongates, to the level of about 20 s$^{-1}$ to 100 s$^{-1}$ according to Bazilevsky et al., *Liquid Filament Microrheometer and Some of its Applications*, Proceedings of the 3rd European Rheology Conference, (London, New York 1990a), pp. 41 to 43; and Bazilevsky et al., *Stresses in the Filaments of Polymer Solutions*, Progr. and Trends in Rheology IV. Proc. 4th Europ. Rheol. Conf., (Sevilla, Spain 1994), pp. 468 to 470, and the initial longitudinal stresses relax at a distance of about 2 to about 4 cm from the transition zone at the end of the Taylor cone. These observations of the transition zone from a Taylor cone to a thin jet reveal why the straight section of the electrospinning jets is longer at higher voltage. This is because higher initial stresses are generated in the transition zone at higher applied voltages so the straight jet is stabilized for a longer distance. After that, the electrically driven bending instability, characteristic of electrospinning, can begin and dramatic elongation, somewhat similar to the elongation following the Taylor cone, occurs at rates of about 1000 s$^{-1}$ (Bazilevsky et al., *Liquid Filament Microrheometer and Some of its Applications*, Proceedings of the 3rd European Rheology Conference, (London, New York 1990a), pp. 41 to 43). The results also point to an opportunity to build an elongational rheometer for semi-dilute and concentrated polymer solutions and melts allowing for stretching rates of the order of about 100 s$^{-1}$ to about 1000 s$^{-1}$.

Although the invention has been described in detail with reference to particular examples and embodiments, the examples and embodiments contained herein are merely illustrative and are not an exhaustive list. Variations and modifications of the present invention will readily occur to those skilled in the art. The present invention includes all such modifications and equivalents.

What is claimed is:

1. A method for creating a perturbation in a polymeric fluid to characterize the viscoelastic properties of said polymeric fluid , the method comprising the steps of:
   (A) providing at least one fluid reservoir containing at least one polymeric fluid material;
   (B) applying at least one DC charge to the at least one polymeric fluid material in order to cause the at least one polymeric fluid material to undergo an electrospinning and/or electrodeposition process, forming a straight tapering viscoelastic jet;
   (C) imparting one or more pulse-like bending perturbations to the straight tapering viscoelstic jet of the at least one polymeric fluid material during the electrospinning and/or electrodeposition process; and
   (D) collecting the electrospun and/or electrodeposited polymeric material on a suitable collector.

2. The method of claim 1, wherein Step (C) utilizes at least one device designed to impart one or more pulse-like bending perturbations to the at least one polymeric fluid material during the electrospinning and/or electrodeposition process, and wherein the at least one device is a combination of a speaker and a polymer bar that is placed into contact with the at least one fluid reservoir.

3. The method of claim 1, wherein Step (C) utilizes at least one mechanical device to impart one or more pulse-like bending perturbations to the at least one polymeric fluid material during the electrospinning and/or electrodeposition process.

4. The method of claim 1, wherein Step (C) utilizes at least one laser to impart one or more pulse-like bending perturbations to the at least one polymeric fluid material during the electrospinning and/or electrodeposition process.

5. The method of claim 1, wherein Step (C) utilizes at least one electrical field to impart one or more pulse-like bending perturbations to the at least one polymeric fluid material during the electrospinning and/or electrodeposition process.

6. The method of claim 1, wherein Step (D) utilizes a grounded collector.

7. The method of claim 1, wherein the method further comprises the step of:
   (E) observing the one or more pulse-like bending perturbations in the at least one polymeric fluid material during the electrospinning and/or electrodeposition process.

8. The method of claim 7, wherein Step (E) utilizes a high speed camera.

9. The method of claim 7, wherein Step (E) utilizes a combination of a high speed camera and an illumination source.

10. The method of claim 7, wherein the method further comprises the step of:
   (F) analyzing the observations from the one or more perturbations in the at least one polymeric fluid material during the electrospinning and/or electrodeposition process.

11. A method for producing one or more pulse-like bending perturbations in a polymeric fluid material, the method comprising the steps of:
   (i) providing at least one fluid reservoir containing at least one polymeric fluid material;
   (ii) applying at least one DC charge to the at least one polymeric fluid material in order to cause the at least one polymeric fluid material to undergo an electrospinning and/or electrodeposition process, forming a straight tapering viscoelastic jet;
   (iii) imparting one or more pulse-like bending perturbations to the straight tapering viscoelastic jet of the at least one polymeric fluid material during the electrospinning and/or electrodeposition process;
   (iv) collecting the electrospun and/or electrodeposited polymeric material on a suitable collector;
   (v) observing the one or more pulse-like bending perturbations in the at least one polymeric fluid material during the electrospinning and/or electrodeposition process;
   (vi) analyzing the observations from the one or more pulse-like bending perturbations in the at least one polymeric fluid material during the electrospinning and/or electrodeposition process; and
   (vii) controlling the electrospinning and/or electrodeposition process based on the data analysis of the one or more pulse-like bending perturbations in the at least one polymeric fluid material.

12. The method of claim 11, wherein Step (i) utilizes at least one pipette designed to contain the at least one polymeric fluid material.

13. The method of claim 11, wherein Step (ii) utilizes at least one ammeter designed to measure one or more DC charge.

14. The method of claim 11, wherein Step (iii) utilizes at least one device designed to impart one or more pulse-like bending perturbations to the at least one polymeric fluid material during the electrospinning and/or electrodeposition process, and wherein the at least one device is a combination of a speaker and a polymer bar that is placed into contact with the at least one fluid reservoir.

15. The method of claim 11, wherein Step (iii) utilizes at least one mechanical device to impart one or more pulse-like bending perturbations to the at least one polymeric fluid material during the electrospinning and/or electrodeposition process.

16. The method of claim 11, wherein Step (iii) utilizes at least one laser to impart one or more pulse-like bending perturbations to the at least one polymeric fluid material during the electrospinning and/or electrodeposition process.

17. The method of claim 11, wherein Step (iii) utilizes at least one electrical field to impart one or more pulse-like bending perturbations to the at least one polymeric fluid material during the electrospinning and/or electrodeposition process.

18. The method of claim 11, wherein Step (iv) utilizes a grounded collector.

19. The method of claim 11, wherein Step (v) utilizes a high speed camera.

20. The method of claim 11, wherein Step (v) utilizes a combination of a high speed camera and an illumination source.

21. The method of claim 11, wherein Step (vi) utilizes at least one computer designed to analyze the observations from the one or more pulse-like bending perturbations created in the at least one polymeric fluid material.

22. The method of claim 1, wherein said one or more pulse-like bending perturbations comprise single pulse perturbations or time-periodic perturbations.

23. The method of claim 11, wherein said one or more pulse-like bending perturbations comprise single pulse perturbations or time-periodic perturbations.

* * * * *